United States Patent
Bloodworth

(10) Patent No.: US 6,329,638 B1
(45) Date of Patent: Dec. 11, 2001

(54) HEATING VEST SYSTEM

(76) Inventor: Vicky W. Bloodworth, 102 Lakecrest Dr., Milledgeville, GA (US) 31061

( * ) Notice: Subject to any disclaimer, the term of this patent is extended or adjusted under 35 U.S.C. 154(b) by 0 days.

(21) Appl. No.: 09/659,129

(22) Filed: Sep. 11, 2000

(51) Int. Cl.$^7$ ................ H05B 1/00; A61H 1/00
(52) U.S. Cl. .................. 219/211; 219/527; 601/15; 601/18
(58) Field of Search ............... 219/211, 527, 219/528, 529, 549; 601/15, 18; 429/127

(56) References Cited

U.S. PATENT DOCUMENTS

| | | |
|---|---|---|
| 3,751,620 | 8/1973 | Yuasa . |
| 3,778,590 | 12/1973 | Iizuka et al. . |
| 3,839,621 * | 10/1974 | Hariu ................. 219/211 |
| 4,061,897 | 12/1977 | Thjkeson . |
| 4,607,624 * | 8/1986 | Jefferson ............... 601/18 |
| 4,979,502 * | 12/1990 | Hunt .................. 601/15 |
| 4,985,934 | 1/1991 | Pemy . |
| 5,032,705 * | 7/1991 | Batcheller et al. ........ 219/211 |
| 5,101,515 | 4/1992 | Holt et al. . |
| 5,148,002 * | 9/1992 | Kuo et al. ............ 219/211 |
| 5,302,806 | 4/1994 | Simmons et al. . |
| 5,866,881 * | 2/1999 | Jones, III ............ 219/527 |
| 6,049,062 * | 4/2000 | Jones ................ 219/211 |

* cited by examiner

*Primary Examiner*—Teresa Walberg
*Assistant Examiner*—Vinod D Patel

(57) ABSTRACT

A heat vest system that includes a garment wearable by the user having strategically located vibration and heating elements which is worn by the user such that the heating and vibration elements are correctly positioned for a therapeutic effect. To increase the therapeutic effect, the system includes a control device in connection with the vibration and heating elements of the garment which allows the user to separately adjust the heat and vibration generated by each of the heating and vibration elements.

1 Claim, 2 Drawing Sheets

HEATING VEST SYSTEM

TECHNICAL FIELD

The present invention relates to heating and vibrating appliances and more particularly to a heating vest system that includes a vest assembly, a control panel and a DC power source; the vest assembly including a back vibrating heating pad structure, a left shoulder vibrating heating pad structure, a right shoulder vibrating heating pad structure, and a neck vibrating heating pad structure; the control panel having separate heat and vibration controls for each of the back, left shoulder, right shoulder and neck vibrating heating pad structures; the control panel controlling power flow between the DC power supply source and the vibrating and heating elements of the back, left should, right shoulder and vibrating heating pad structures; the neck vibrating heating pad structure being detachably mechanically connectable to an upper edge of the back vibrating heating pad structure; the left shoulder vibrating heating pad structure including a bottom front vest portion having a loop through which a left vest portion securing strap is passed with an attached end of the left vest portion securing strap being mechanically connected to the back vibrating heating pad structure and an adjustable connecter at the other end of left vest portion securing strap; the right shoulder vibrating heating pad structure including a bottom front vest portion having a loop through which a right vest portion securing strap is passed with an attached end of the right vest portion securing strap being mechanically connected to the back vibrating heating pad structure and an adjustable connecter at the other end of right vest portion securing strap; an adjustable connecters at the ends of the left and right vest portion securing straps being adjustably interconnectable to allow the left and right vest portion securing straps to be secured around different sized individuals; the DC power supply source including an AC to DC adapter and a cigarette lighter socket adapter.

BACKGROUND ART

Many individuals suffer from back, shoulder and neck pain that requires the individual to apply heat and vibration to receive a reduction in the pain. Although some areas of the body pose little problem to applying heat and vibration, it can be difficult for some individuals to maintain the heating and vibrating elements in the correct locations while trying to move around even minimally. It would be desirable. Therefore, to have a heat vest system that included a garment wearable by the user having strategically located vibration and heating elements which could be put on by the user such that the heating and vibration elements are correctly positioned for a therapeutic effect. To increase the therapeutic effect, it would be desirable to have a control device in connection with the vibration and heating elements of the garment which allowed the user to separately adjust the heat and vibration generated by each of the heating and vibration elements.

GENERAL SUMMARY DISCUSSION OF INVENTION

It is thus an object of the invention to provide a heating vest system that includes a vest assembly, a control panel and a DC power source; the vest assembly including a back vibrating heating pad structure, a left shoulder vibrating heating pad structure, a right shoulder vibrating heating pad structure, and a neck vibrating heating pad structure; the control panel having separate heat and vibration controls for each of the back, left shoulder, right shoulder and neck vibrating heating pad structures; the control panel controlling power flow between the DC power supply source and the vibrating and heating elements of the back, left should, right shoulder and vibrating heating pad structures; the neck vibrating heating pad structure being detachably mechanically connectable to an upper edge of the back vibrating heating pad structure; the left shoulder vibrating heating pad structure including a bottom front vest portion having a loop through which a left vest portion securing strap is passed with an attached end of the left vest portion securing strap being mechanically connected to the back vibrating heating pad structure and an adjustable connecter at the other end of left vest portion securing strap; the right shoulder vibrating heating pad structure including a bottom front vest portion having a loop through which a right vest portion securing strap is passed with an attached end of the right vest portion securing strap being mechanically connected to the back vibrating heating pad structure and an adjustable connecter at the other end of right vest portion securing strap; an adjustable connecters at the ends of the left and right vest portion securing straps being adjustably interconnectable to allow the left and right vest portion securing straps to be secured around different sized individuals; the DC power supply source including an AC to DC adapter and a cigarette lighter socket adapter.

Accordingly, a heating vest system is provided. The heating vest system includes a vest assembly, a control panel and a DC power source; the vest assembly including a back vibrating heating pad structure, a left shoulder vibrating heating pad structure, a right shoulder vibrating heating pad structure, and a neck vibrating heating pad structure; the control panel having separate heat and vibration controls for each of the back, left shoulder, right shoulder and neck vibrating heating pad structures; the control panel controlling power flow between the DC power supply source and the vibrating and heating elements of the back, left should, right shoulder and vibrating heating pad structures; the neck vibrating heating pad structure being detachably mechanically connectable to an upper edge of the back vibrating heating pad structure; the left shoulder vibrating heating pad structure including a bottom front vest portion having a loop through which a left vest portion securing strap is passed with an attached end of the left vest portion securing strap being mechanically connected to the back vibrating heating pad structure and an adjustable connecter at the other end of left vest portion securing strap; the right shoulder vibrating heating pad structure including a bottom front vest portion having a loop through which a right vest portion securing strap is passed with an attached end of the right vest portion securing strap being mechanically connected to the back vibrating heating pad structure and an adjustable connecter at the other end of right vest portion securing strap; an adjustable connecters at the ends of the left and right vest portion securing straps being adjustably interconnectable to allow the left and right vest portion securing straps to be secured around different sized individuals; the DC power supply source including an AC to DC adapter and a cigarette lighter socket adapter.

BRIEF DESCRIPTION OF DRAWINGS

For a further understanding of the nature and objects of the present invention, reference should be made to the following detailed description, taken in conjunction with the accompanying drawings, in which like elements are given the same or analogous reference numbers and wherein.

EXEMPLARY MODE FOR CARRYING OUT THE INVENTION

Figure 1:
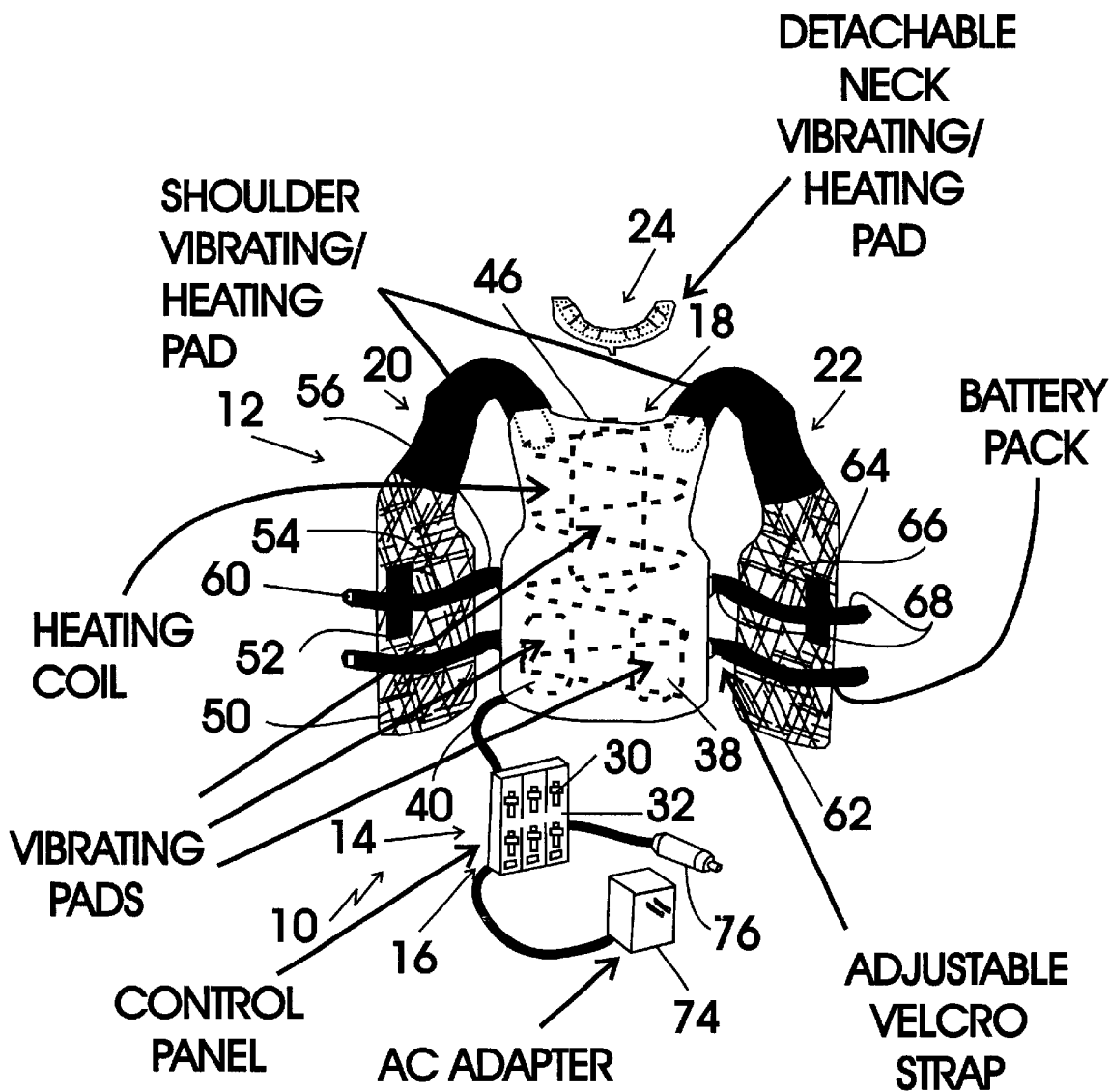
FIG. 1 is a backside, perspective view of the heating vest system of the present invention showing a heating vest system including a vest assembly, a control panel and a DC power source; the vest assembly including a back vibrating heating pad structure, a left shoulder vibrating heating pad structure, a right shoulder vibrating heating pad structure, and a neck vibrating heating pad structure; the control panel having separate heat and vibration controls for each of the back, left shoulder, right shoulder and neck vibrating heating pad structures; the control panel controlling power flow between a DC power supply source and the vibrating and heating elements of the back, left should, right shoulder and vibrating heating pad structures; the neck vibrating heating pad structure being detachably mechanically connectable to an upper edge of the back vibrating heating pad structure; the left shoulder vibrating heating pad structure including a bottom front vest portion having a loop through which a left vest portion securing strap is passed with an attached end of the left vest portion securing strap being mechanically connected to the back vibrating heating pad structure and an adjustable connecter at the other end of left vest portion securing strap; the right shoulder vibrating heating pad structure including a bottom front vest portion having a loop through which a right vest portion securing strap is passed with an attached end of the right vest portion securing strap being mechanically connected to the back vibrating heating pad structure and an adjustable connecter at the other end of right vest portion securing strap; an adjustable connecters at the ends of the left and right vest portion securing straps being adjustably interconnectable to allow the left and right vest portion securing straps to be secured around different sized individuals; the DC power supply source including an AC to DC adapter and a cigarette lighter socket adapter.
Figure 2:
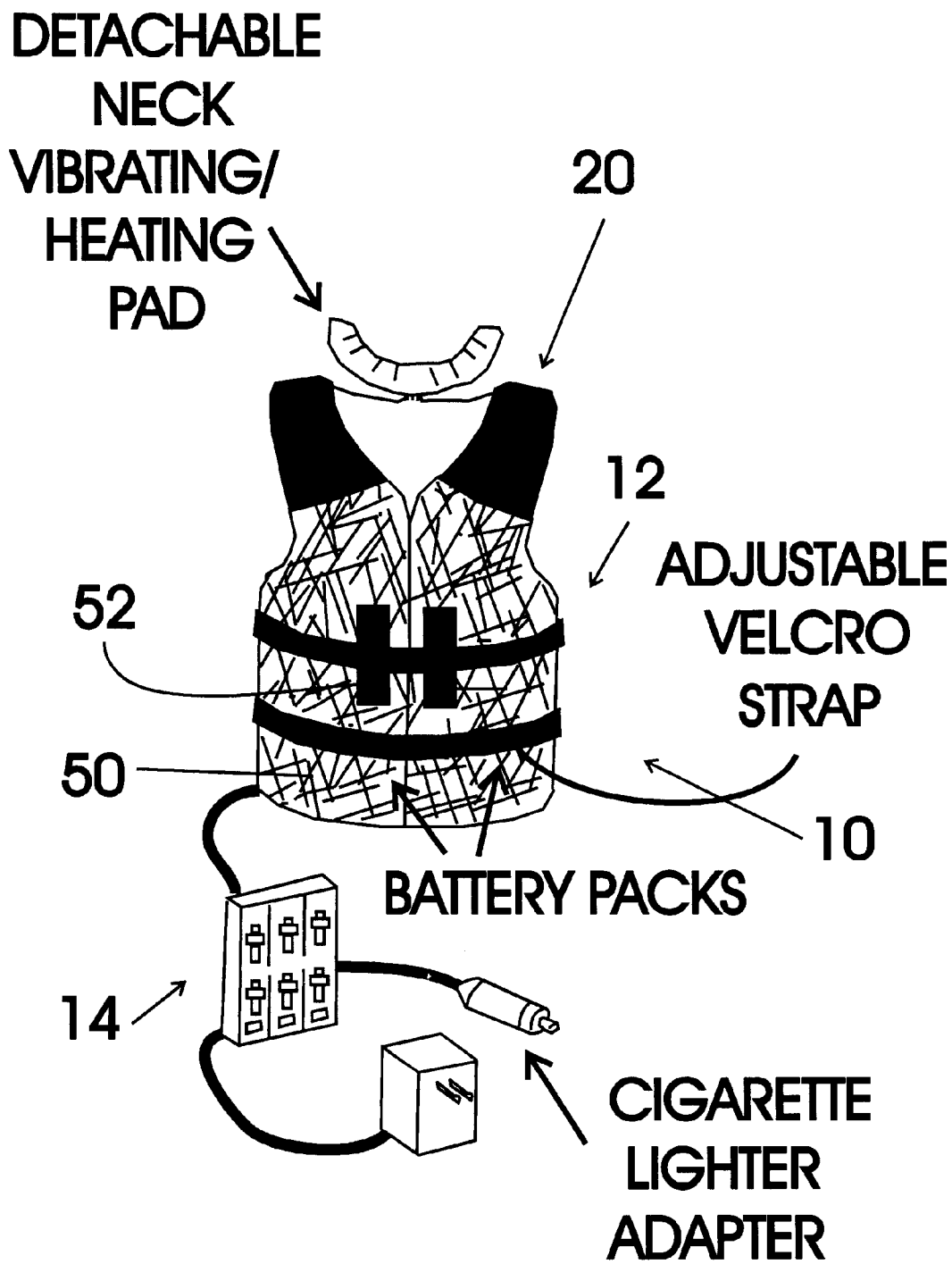
FIG. 2 is a perspective view of the front side of the heating vest system of FIG. 1 showing the vest assembly secured in the closed position.

FIGS. 1 and 2 show various aspects of an exemplary embodiment of the heating vest system of the present invention generally designated 10. Heating vest system 10 includes a vest assembly, generally designated 12; a control panel, generally designated 14; and a DC power source, generally designated 16.

Vest assembly 12 includes a back vibrating heating pad structure, generally designated 18; a left shoulder vibrating heating pad structure, generally designated 20; a right shoulder vibrating heating pad structure, generally designated 22 and a detachably connectable neck vibrating heating pad structure, generally designated 24. Control panel 14 has separate heat and vibration controls 30, 32 for each of the back 18, left shoulder 20, right shoulder 22 and neck vibrating heating pad structures 24 plus two additional sets of controls 30, 32 for addition items. Control panel 14 controls power flow between the DC power supply source 16 and the vibrating elements 40 and heating elements 30 of the back 18, left shoulder 20, right shoulder 22 and neck 24 vibrating heat pad structures. Neck vibrating heating pad structure 24 is detachably mechanically connectable to an upper edge 46 of back vibrating heating pad structure 18. Left shoulder vibrating heating pad structure 20 includes a bottom front vest portion 50 having a loop 52 through which a left vest portion securing strap 54 is passed with an attached end 56 of left vest portion securing strap 54 mechanically connected to back vibrating heating pad structure 18 and an adjustable connecter 60 at the other end of left vest portion securing strap 54. Right shoulder vibrating heating pad structure 22 includes a bottom front vest portion 62 having a loop 64 through which a right vest portion securing strap 66 is passed with an attached end 68 of right vest portion securing strap 66 mechanically connected to back vibrating heating pad structure 18 and an adjustable connecter 68 at the other end of right vest portion securing strap 66. Adjustable connecters 60 and 68 at the ends of the left and right vest portion securing straps 54, 66 are adjustably interconnectable to allow the left and right vest portion securing straps 54, 66 to be secured around different sized individuals. DC power supply source 16 includes an AC to DC adapter 74 for use while at home or the like and a cigarette lighter socket adapter 76 for use while traveling in a vehicle or the like.

It can be seen from the preceding description that a heating vest system has been provided.

It is noted that the embodiment of the heating vest system described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. a heating vest system comprising:

a vest assembly;

a control panel; and a DC power source;

the vest assembly including a back vibrating heating pad structure, a left shoulder vibrating heating pad structure, a right shoulder vibrating heating pad structure, and a neck vibrating heating pad structure;

the control panel having separate heat and vibration controls for each of the back, left shoulder, right shoulder and neck vibrating heating pad structures;

the control panel controlling power flow between the DC power supply source and the vibrating and heating elements of the back, left shoulder right shoulder and vibrating heating pad structures;

the neck vibrating heating pad structure being detachably mechanically connectable to an upper edge of the back vibrating heating pad structure;

the left shoulder vibrating heating pad structure including a bottom front vest portion having a loop through which a left vest portion securing strap is passed with an attached end of the left vest portion securing strap being mechanically connected to the back vibrating heating pad structure and an adjustable connecter at the other end of left vest portion securing strap;

the right shoulder vibrating heating pad structure including a bottom front vest portion having a loop through which a right vest portion securing strap is passed with an attached end of the right vest portion securing strap being mechanically connected to the back vibrating heating pad structure and an adjustable connecter at the other end of right vest portion securing strap;

the adjustable connecters at the ends of the left and right vest portion securing straps being adjustable interconnectable to allow the left and right vest portion securing straps to be secured around different sized individuals;

the DC power supply source including an AC to DC adapter and a cigarette lighter socket adapter.

* * * * *